US012551654B2

(12) United States Patent
Mihelich

(10) Patent No.: US 12,551,654 B2
(45) Date of Patent: Feb. 17, 2026

(54) COMPRESSION RESISTANT SHEATH

(71) Applicant: BOSTON SCIENTIFIC SCIMED, INC., Maple Grove, MN (US)

(72) Inventor: Benjamin Mihelich, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1141 days.

(21) Appl. No.: 17/496,959

(22) Filed: Oct. 8, 2021

(65) Prior Publication Data

US 2022/0126058 A1 Apr. 28, 2022

Related U.S. Application Data

(60) Provisional application No. 63/104,007, filed on Oct. 22, 2020.

(51) Int. Cl.
*A61M 25/00* (2006.01)

(52) U.S. Cl.
CPC ...... *A61M 25/005* (2013.01); *A61M 25/0012* (2013.01); *A61M 2025/0059* (2013.01); *A61M 2025/0098* (2013.01); *A61M 2205/0216* (2013.01)

(58) Field of Classification Search
CPC ............ A61M 25/005; A61M 25/0012; A61M 2025/0059; A61M 2025/0098; A61M 2205/0216
See application file for complete search history.

(56) References Cited

U.S. PATENT DOCUMENTS

| | | | | |
|---|---|---|---|---|
| 3,416,531 A | | 12/1968 | Edwards | |
| 4,276,874 A | * | 7/1981 | Wolvek ............. | A61M 25/0054 604/914 |
| 4,676,229 A | * | 6/1987 | Krasnicki .............. | A61B 1/042 600/153 |
| 5,290,230 A | | 3/1994 | Ainsworth et al. | |

(Continued)

FOREIGN PATENT DOCUMENTS

| | | |
|---|---|---|
| EP | 2174685 B1 | 8/2012 |
| EP | 2572749 A2 | 3/2013 |

(Continued)

OTHER PUBLICATIONS

U.S. Appl. No. 62/899,844, filed Sep. 13, 2019.
International Search Report and Written Opinion dated Feb. 25, 2022 for International Application No. PCT/US2021/054168.

*Primary Examiner* — James D Ponton
*Assistant Examiner* — John A Doubrava
(74) *Attorney, Agent, or Firm* — Seager, Tufte & Wickhem LLP

(57) ABSTRACT

An elongate tubular shaft having a lumen extending from a proximal portion to a distal portion may include an outer jacket forming an outer surface of the elongate tubular shaft, the outer jacket being formed from a first material having a first modulus of elasticity, a helical member extending from the proximal portion to the distal portion, a braided support member disposed about the helical member, and a strain relief layer formed from a second material having a second modulus of elasticity less than the first modulus of elasticity, wherein the strain relief layer is disposed about the helical member and radially inward of the outer jacket.

11 Claims, 11 Drawing Sheets

(56) References Cited

U.S. PATENT DOCUMENTS 5,356,388 A 10/1994 Sepetka et al.
5,382,259 A 1/1995 Phelps et al.
5,415,664 A 5/1995 Pinchuk
5,522,822 A 6/1996 Phelps et al.
5,562,619 A 10/1996 Mirarchi et al.
5,603,694 A 2/1997 Brown et al.
5,653,684 A 8/1997 Laptewicz et al.
5,676,653 A 10/1997 Taylor et al.
5,702,433 A 12/1997 Taylor et al.
5,843,076 A 12/1998 Webster et al.
5,865,800 A 2/1999 Mirarchi et al.
5,897,529 A 4/1999 Ponzi
5,964,757 A 10/1999 Ponzi
6,080,117 A 6/2000 Cornelius
6,096,052 A 8/2000 Callister et al.
6,120,476 A 9/2000 Fung et al.
6,210,362 B1 4/2001 Ponzi
6,210,407 B1 4/2001 Webster
6,210,476 B1 4/2001 Chatterji et al.
6,308,090 B1 10/2001 Tu et al.
6,328,702 B1 12/2001 Cornelius
6,338,736 B1 1/2002 Boosfeld et al.
6,375,670 B1 4/2002 Greenhalgh
6,398,758 B1 6/2002 Jacobsen et al.
6,402,719 B1 6/2002 Ponzi et al.
6,402,771 B1 6/2002 Palmer et al.
6,432,116 B1 8/2002 Callister et al.
6,478,777 B1 11/2002 Honeck et al.
6,494,907 B1 12/2002 Bulver
6,602,242 B1 8/2003 Fung et al.
6,648,874 B2 11/2003 Parisi et al.
6,818,006 B2 11/2004 Douk et al.
6,866,677 B2 3/2005 Douk et al.
6,890,329 B2 5/2005 Carroll et al.
6,926,711 B2 8/2005 Lentz et al.
7,066,946 B2 6/2006 Douk et al.
7,089,065 B2 8/2006 Westlund et al.
7,419,477 B2 9/2008 Simpson et al.
7,572,274 B2 8/2009 Yassinzadeh
7,774,039 B2 8/2010 Koblish
7,862,577 B2 1/2011 Gray et al.
7,914,466 B2 3/2011 Davis et al.
7,955,298 B2 6/2011 Carroll et al.
8,066,664 B2 11/2011 Laduca et al.
8,109,946 B2 2/2012 Cahill et al.
8,229,538 B2 7/2012 Koblish
8,376,991 B2 2/2013 Kauphusman et al.
8,409,273 B2 4/2013 Thornton et al.
8,423,115 B2 4/2013 Koblish
8,585,858 B2 11/2013 Kronfeld et al.
8,608,703 B2 12/2013 Riles et al.
8,632,584 B2 1/2014 Henkes et al.
8,668,668 B2 3/2014 Bishop et al.
8,676,341 B2 3/2014 Kane et al.
8,700,120 B2 4/2014 Koblish
8,771,294 B2 7/2014 Sepetka et al.
8,934,991 B2 1/2015 Kane et al.
8,983,574 B2 3/2015 Schmidt et al.
9,044,577 B2 6/2015 Bishop et al.
9,186,152 B2 11/2015 Campbell et al.
9,248,255 B2 2/2016 Selkee
9,339,630 B2 5/2016 Cook et al.
9,393,021 B2 7/2016 Garcia et al.
9,486,606 B2 11/2016 Schaeffer
9,486,612 B2 11/2016 Kauphusman et al.
9,585,587 B2 3/2017 Roy et al.
9,687,245 B2 6/2017 Molaei et al.
10,071,223 B2 9/2018 Anderson
10,105,516 B2 10/2018 Selkee
10,258,730 B2 4/2019 Franano et al.
10,456,161 B2 10/2019 Steele
10,653,862 B2 5/2020 Winston et al.
10,661,052 B2 5/2020 Mcniven et al.
10,675,444 B2 6/2020 Kauphusman et al.
10,729,445 B2 8/2020 Wallace et al.
2001/0003297 A1 6/2001 Pedersen et al.
2001/0009986 A1 7/2001 Ponzi
2001/0016728 A1 8/2001 Kelley
2001/0016730 A1 8/2001 Martins et al.
2001/0027310 A1 10/2001 Parisi et al.
2001/0041900 A1 11/2001 Callister et al.
2002/0029051 A1 3/2002 Callister et al.
2002/0072764 A1 6/2002 Sepetka et al.
2002/0082585 A1 6/2002 Carroll et al.
2002/0099435 A1 7/2002 Stinson
2002/0133141 A1 9/2002 Sparks et al.
2002/0143360 A1 10/2002 Douk et al.
2002/0151927 A1 10/2002 Douk et al.
2002/0161395 A1 10/2002 Douk et al.
2003/0055374 A1 3/2003 Martins et al.
2003/0097064 A1 5/2003 Talpade et al.
2003/0195553 A1 10/2003 Wallace et al.
2003/0199921 A1 10/2003 Palmer et al.
2004/0122473 A1 6/2004 Ewers et al.
2004/0127918 A1 7/2004 Nikolchev et al.
2004/0167604 A1 8/2004 Stinson
2004/0186506 A1 9/2004 Simpson et al.
2005/0027334 A1 2/2005 Lentz et al.
2005/0149176 A1 7/2005 Heggestuen et al.
2005/0159770 A1 7/2005 Divani et al.
2005/0172972 A1 8/2005 Nikolchev et al.
2005/0209557 A1 9/2005 Carroll et al.
2005/0217680 A1 10/2005 Callister et al.
2005/0251031 A1 11/2005 Smith
2006/0178739 A1 8/2006 Shalaby et al.
2006/0189896 A1 8/2006 Davis et al.
2006/0206200 A1 9/2006 Garcia et al.
2006/0253184 A1 11/2006 Amplatz
2007/0043430 A1 2/2007 Stinson
2007/0106311 A1 5/2007 Wallace et al.
2007/0118207 A1 5/2007 Amplatz et al.
2007/0123851 A1 5/2007 Alejandro et al.
2007/0250081 A1 10/2007 Cahill et al.
2007/0270679 A1 11/2007 Nguyen et al.
2007/0276324 A1 11/2007 Laduca et al.
2008/0045895 A1 2/2008 Simpson et al.
2008/0076999 A1 3/2008 Koblish
2008/0154303 A1 6/2008 Yassinzadeh
2008/0208043 A1 8/2008 Smith et al.
2008/0312671 A1 12/2008 Riles et al.
2009/0025820 A1 1/2009 Adams
2009/0112239 A1 4/2009 To
2009/0275971 A1 11/2009 Kelleher et al.
2009/0287182 A1 11/2009 Bishop et al.
2009/0287183 A1 11/2009 Bishop et al.
2009/0299333 A1* 12/2009 Wendlandt .......... A61M 25/005 604/527
2010/0145267 A1 6/2010 Bishop et al.
2010/0185271 A1 7/2010 Zhang
2010/0286499 A1 11/2010 Koblish
2010/0286626 A1 11/2010 Petersen et al.
2011/0144690 A1 6/2011 Bishop et al.
2011/0166592 A1 7/2011 Garcia et al.
2011/0196413 A1 8/2011 Wallace et al.
2011/0315301 A1 12/2011 Simpson et al.
2012/0041466 A1 2/2012 Bishop et al.
2012/0059448 A1 3/2012 Parker et al.
2012/0109078 A1* 5/2012 Schaeffer .......... A61M 25/0012 604/264
2012/0116200 A1 5/2012 Roy et al.
2012/0172927 A1 7/2012 Campbell et al.
2012/0277671 A1 11/2012 Fuentes
2012/0289939 A1 11/2012 Koblish
2012/0310213 A1 12/2012 Kronfeld et al.
2012/0316429 A1 12/2012 Schmidt et al.
2012/0316638 A1 12/2012 Grad et al.
2012/0330354 A1 12/2012 Kane et al.
2013/0158479 A1 6/2013 Kauphusman et al.
2013/0253572 A1 9/2013 Molaei et al.
2013/0296780 A1 11/2013 Tegg
2014/0074149 A1 3/2014 Garcia et al.
2014/0081365 A1 3/2014 Kane et al.
2014/0135687 A1 5/2014 Selkee
2014/0135810 A1 5/2014 Divino et al.

(56) References Cited

U.S. PATENT DOCUMENTS

| | | | |
|---|---|---|---|
| 2014/0135812 A1 | 5/2014 | Divino et al. | |
| 2014/0296615 A1 | 10/2014 | Franano | |
| 2014/0343585 A1 | 11/2014 | Ferrera et al. | |
| 2015/0216688 A1 | 8/2015 | Landsman et al. | |
| 2015/0352327 A1 | 12/2015 | Helgeson et al. | |
| 2016/0001040 A1 | 1/2016 | Yamaguchi et al. | |
| 2016/0121075 A1 | 5/2016 | Schaeffer | |
| 2016/0121078 A1 | 5/2016 | Anderson | |
| 2016/0144153 A1 | 5/2016 | Selkee | |
| 2016/0175569 A1 | 6/2016 | Heuser | |
| 2016/0220265 A1 | 8/2016 | Pokorney et al. | |
| 2017/0035430 A1 | 2/2017 | Sarge et al. | |
| 2017/0056616 A1 | 3/2017 | Leeflang et al. | |
| 2017/0136213 A1 | 5/2017 | Kauphusman et al. | |
| 2017/0189215 A1 | 7/2017 | Merlo et al. | |
| 2017/0224355 A1 | 8/2017 | Bowman et al. | |
| 2017/0245864 A1 | 8/2017 | Franano et al. | |
| 2017/0258981 A1 | 9/2017 | Franano et al. | |
| 2017/0296222 A1 | 10/2017 | Steele | |
| 2018/0015257 A1 | 1/2018 | Krolik et al. | |
| 2018/0028177 A1 | 2/2018 | Van Oepen et al. | |
| 2018/0116843 A1 | 5/2018 | Schreck et al. | |
| 2018/0126119 A1* | 5/2018 | McNiven .......... | A61M 25/0136 |
| 2018/0126124 A1 | 5/2018 | Winston et al. | |
| 2018/0250013 A1 | 9/2018 | Wallace et al. | |
| 2018/0344982 A1 | 12/2018 | Tegg | |
| 2019/0053925 A1 | 2/2019 | Lonn et al. | |
| 2019/0054277 A1 | 2/2019 | Labelle et al. | |
| 2019/0105469 A1 | 4/2019 | Helgeson et al. | |
| 2019/0217075 A1 | 7/2019 | Beach | |
| 2019/0336313 A1 | 11/2019 | Ferrera et al. | |
| 2019/0343532 A1 | 11/2019 | Divino et al. | |
| 2019/0380739 A1 | 12/2019 | Steele | |
| 2019/0388218 A1 | 12/2019 | Vidlund et al. | |
| 2019/0388220 A1 | 12/2019 | Vidlund et al. | |
| 2020/0061337 A1 | 2/2020 | Singh et al. | |
| 2020/0061362 A1 | 2/2020 | Singh et al. | |
| 2020/0078560 A1 | 3/2020 | Tegg et al. | |
| 2020/0100795 A1 | 4/2020 | Connor | |
| 2020/0107842 A1 | 4/2020 | Greenhalgh et al. | |
| 2020/0155804 A1 | 5/2020 | Von Oepen et al. | |
| 2020/0179652 A1 | 6/2020 | Williams et al. | |
| 2020/0230352 A1 | 7/2020 | McNiven et al. | |
| 2021/0046279 A1* | 2/2021 | Bouasaysy .......... | A61M 25/005 |

FOREIGN PATENT DOCUMENTS

| | | |
|---|---|---|
| WO | 2005120622 A2 | 12/2005 |
| WO | 2010115163 A1 | 10/2010 |
| WO | 2010115163 A9 | 7/2011 |
| WO | 2014140093 A1 | 9/2014 |
| WO | 2015186692 A1 | 12/2015 |
| WO | 2017180639 A1 | 10/2017 |
| WO | 2018064325 A1 | 4/2018 |

* cited by examiner

COMPRESSION RESISTANT SHEATH

CROSS-REFERENCE TO RELATED APPLICATIONS

This application claims the benefit of priority of U.S. Provisional Application No. 63/104,007 filed Oct. 22, 2020, the entire disclosure of which is hereby incorporated by reference.

TECHNICAL FIELD

The invention relates generally to medical devices and more particularly to sheaths and/or elongate tubular shafts having improved compression resistance.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. There is an ongoing need to provide alternative medical devices as well as alternative methods for manufacturing and/or using medical devices.

SUMMARY

The disclosure is directed to several alternative designs, materials, and methods of manufacturing a sheath and/or an elongate tubular shaft.

In a first example, an elongate tubular shaft having a lumen extending from a proximal portion to a distal portion may comprise: an outer jacket forming an outer surface of the elongate tubular shaft, the outer jacket being formed from a first material having a first modulus of elasticity; a helical member extending from the proximal portion to the distal portion; a braided support member disposed about the helical member; and a strain relief layer formed from a second material having a second modulus of elasticity less than the first modulus of elasticity. The strain relief layer may be disposed about the helical member and radially inward of the outer jacket.

Alternatively or additionally to any of the examples disclosed herein, the braided support member is embedded within the strain relief layer.

Alternatively or additionally to any of the examples disclosed herein, the helical member defines the lumen.

Alternatively or additionally to any of the examples disclosed herein, the helical member is a tightly wound coil.

Alternatively or additionally to any of the examples disclosed herein, adjacent windings of the helical member are in physical contact with each other.

Alternatively or additionally to any of the examples disclosed herein, the braided support member is in direct contact with the helical member.

Alternatively or additionally to any of the examples disclosed herein, the braided support member prevents relative radial movement of adjacent windings of the helical member with respect to a central longitudinal axis of the elongate tubular shaft.

Alternatively or additionally to any of the examples disclosed herein, the helical member is formed from a metallic material.

Alternatively or additionally to any of the examples disclosed herein, the outer jacket is spaced apart from the braided support member and the helical member by the strain relief layer.

Alternatively or additionally to any of the examples disclosed herein, the elongate tubular shaft is devoid of the strain relief layer radially inward of the helical member.

Alternatively or additionally to any of the examples disclosed herein, an elongate tubular shaft having a lumen extending from a proximal portion to a distal portion may comprise: an outer jacket forming an outer surface of the elongate tubular shaft, the outer jacket being formed from a first material; a helical member extending axially about a central longitudinal axis of the elongate tubular shaft from the proximal portion to the distal portion, wherein a radially inward facing surface of the helical member defines the lumen; a braided support member disposed on an outer surface of the helical member; and a strain relief layer formed from a second material different from the first material. The strain relief layer may be disposed about the helical member and radially inward of the outer jacket.

Alternatively or additionally to any of the examples disclosed herein, the second material is more elastic than the first material.

Alternatively or additionally to any of the examples disclosed herein, adjacent windings of the helical member are in direct contact with each other.

Alternatively or additionally to any of the examples disclosed herein, at least a portion of the strain relief layer is disposed between portions of adjacent windings of the helical member that are disposed radially outward of portions of the adjacent windings that are in direct contact with each other.

Alternatively or additionally to any of the examples disclosed herein, a method of making an elongate tubular shaft having a lumen extending from a proximal portion to a distal portion may comprise: positioning a helical member onto an elongate mandrel with adjacent windings of the helical member in direct contact with each other; interweaving a braided support member on an outer surface of the helical member; disposing an elastomeric material over the braided support member to form a strain relief layer; and disposing an outer jacket over the strain relief layer, the outer jacket being formed of a different material than the strain relief layer.

Alternatively or additionally to any of the examples disclosed herein, the helical member is self-biased toward an axially compressed configuration.

Alternatively or additionally to any of the examples disclosed herein, disposing the elastomeric material over the braided support member includes melting the elastomeric material such that the elastomeric material flows through interstices of the braided support member.

Alternatively or additionally to any of the examples disclosed herein, disposing the outer jacket over the strain relief layer includes bonding the outer jacket to the strain relief layer.

Alternatively or additionally to any of the examples disclosed herein, after disposing the outer jacket over the strain relief layer, no radial space is present between the strain relief layer and the outer jacket.

Alternatively or additionally to any of the examples disclosed herein, the elongate tubular shaft is devoid of the elastomeric material radially inward of the helical member.

The above summary of some example embodiments is not intended to describe each disclosed embodiment or every implementation of the invention.

BRIEF DESCRIPTION OF THE DRAWINGS

The disclosure may be more completely understood in consideration of the following detailed description of various embodiments in connection with the accompanying drawings, in which.

Figure 1:
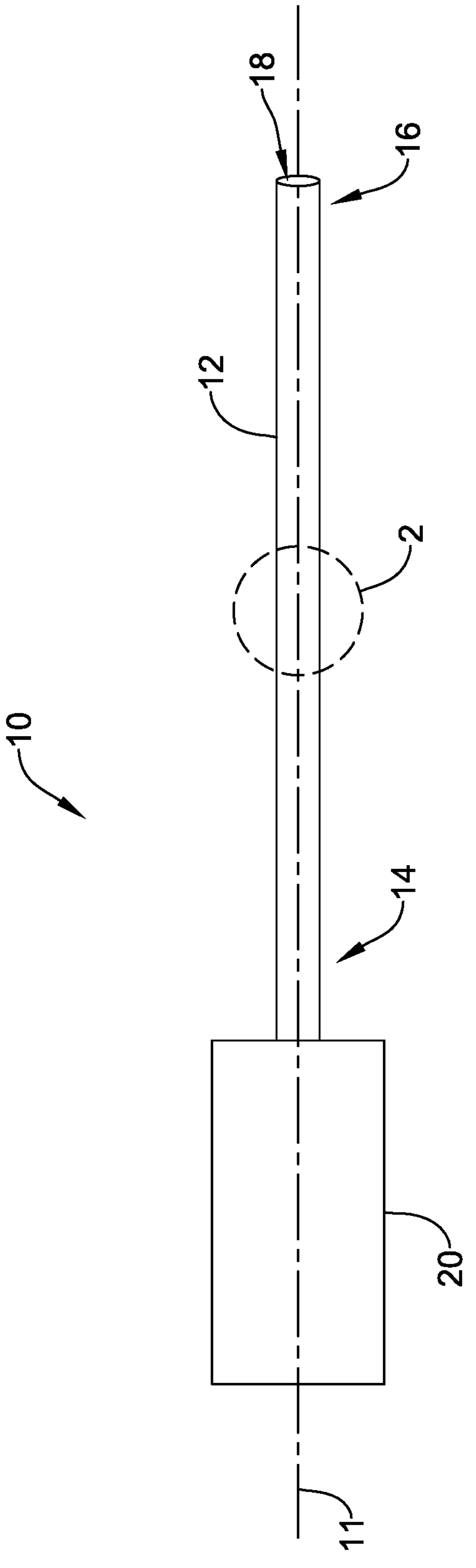
FIG. 1 illustrates selected aspects of an example sheath.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The terms "extent" and/or "maximum extent" may be understood to mean a greatest measurement of a stated or identified dimension, while the term "minimum extent" may be understood to mean a smallest measurement of a stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" or "maximum extent" may be considered a greatest possible dimension measured according to the intended usage. Alternatively, a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

To achieve a required resistance to axial compression, a required resistance to axial shortening, and/or to maintain kink resistance in thin walled polymer catheters or sheaths, the catheter, sheath, or other elongate tubular shaft may be constructed or reinforced with high modulus components to increase their hoop strength and/or axial stiffness. However, with resistance to axial compression and/or axial shortening generally comes increased stiffness and/or reduced flexibility. When navigating tortuous vasculature, for example, flexibility may be considered a very important characteristic. However, with increased flexibility generally comes reduced resistance to axial compression. When a catheter or sheath undergoes axial compression, one or more of several resulting conditions may occur. In no particular order of importance, the axially compressed catheter or sheath may shorten and/or may develop an internal spring force that could release quickly (causing the catheter or sheath to quickly return to its original length) when the compressive force is removed, the axially compressed catheter or sheath may bend and/or may develop an internal whipping force that could release quickly (causing the free or distal end of the catheter or sheath to "whip" and/or snap back toward a straightened condition), one or more layers or materials of the axially compressed catheter or sheath may fracture, the axially compressed catheter or sheath may kink, etc. Generally, these conditions are considered undesirable and/or may produce undesirable consequences. The current disclosure details design configurations that improve resistance to axial compression while substantially maintaining desired flexibility characteristics that are beneficial to anatomical tracking, navigation, and user satisfaction.

FIG. 1 illustrates selected aspects of a sheath 10. In some embodiments, the sheath 10 may be any one of a variety of catheters, such as an intravascular catheter. Examples of intravascular catheters may include, but are not limited to, balloon catheters, atherectomy catheters, device delivery catheters, drug delivery catheters, diagnostic catheters, and guide catheters. In some embodiments, the sheath 10 may take the form of other suitable guiding, diagnosing, or treating devices (including endoscopic instruments, laparoscopic instruments, etc., and the like) and it may be suitable for use at various locations and/or body lumens within a patient. In some embodiments, the sheath 10 may be sized in accordance with its intended use. For example, the sheath 10 can have a length that is in the range of about 50 to about 200 centimeters, about 75 to about 175 centimeters, or about 100 to about 150 centimeters. Other lengths are also contemplated. It is further contemplated that the outer diameter of the sheath 10 may vary based on the use or application.

In some embodiments, the sheath 10 may include an elongate tubular shaft 12 having a lumen 18 extending from a proximal portion 14 to a distal portion 16 along a central longitudinal axis 11 of the elongate tubular shaft 12. In some embodiments, the lumen 18 may extend from a proximal end of the elongate tubular shaft 12 to a distal end of the elongate tubular shaft 12. In some embodiments, the lumen may extend proximally from the distal end and/or the distal portion 16 of the elongate tubular shaft 12 to the proximal portion 14 of the elongate tubular shaft 12. In some embodiments, the lumen 18 may extend an entire length of the elongate tubular shaft 12. In some embodiments, the sheath 10 may include a proximal structure 20 disposed at the proximal end of the elongate tubular shaft 12. In some embodiments, the proximal end and/or the proximal portion 14 of the elongate tubular shaft 12 may be fixedly attached to a distal end of the proximal structure 20. In some embodiments, the elongate tubular shaft 12 may extend proximally into the proximal structure 20. In some embodiments, the proximal structure 20 may include a hub, a strain relief assembly, a handle and/or handle assembly, one or more ports, and/or another suitable structure depending upon the intended use of the sheath 10.

While not explicitly shown, the elongate tubular shaft 12 can include one or more shaft segments having varying degrees of flexibility. In some cases, the elongate tubular shaft 12 may be progressively more flexible toward the distal end of the elongate tubular shaft 12, although this is not required. It is contemplated that the stiffness and size of the elongate tubular shaft 12 may be modified for use in various locations within the body.

Figure 2:
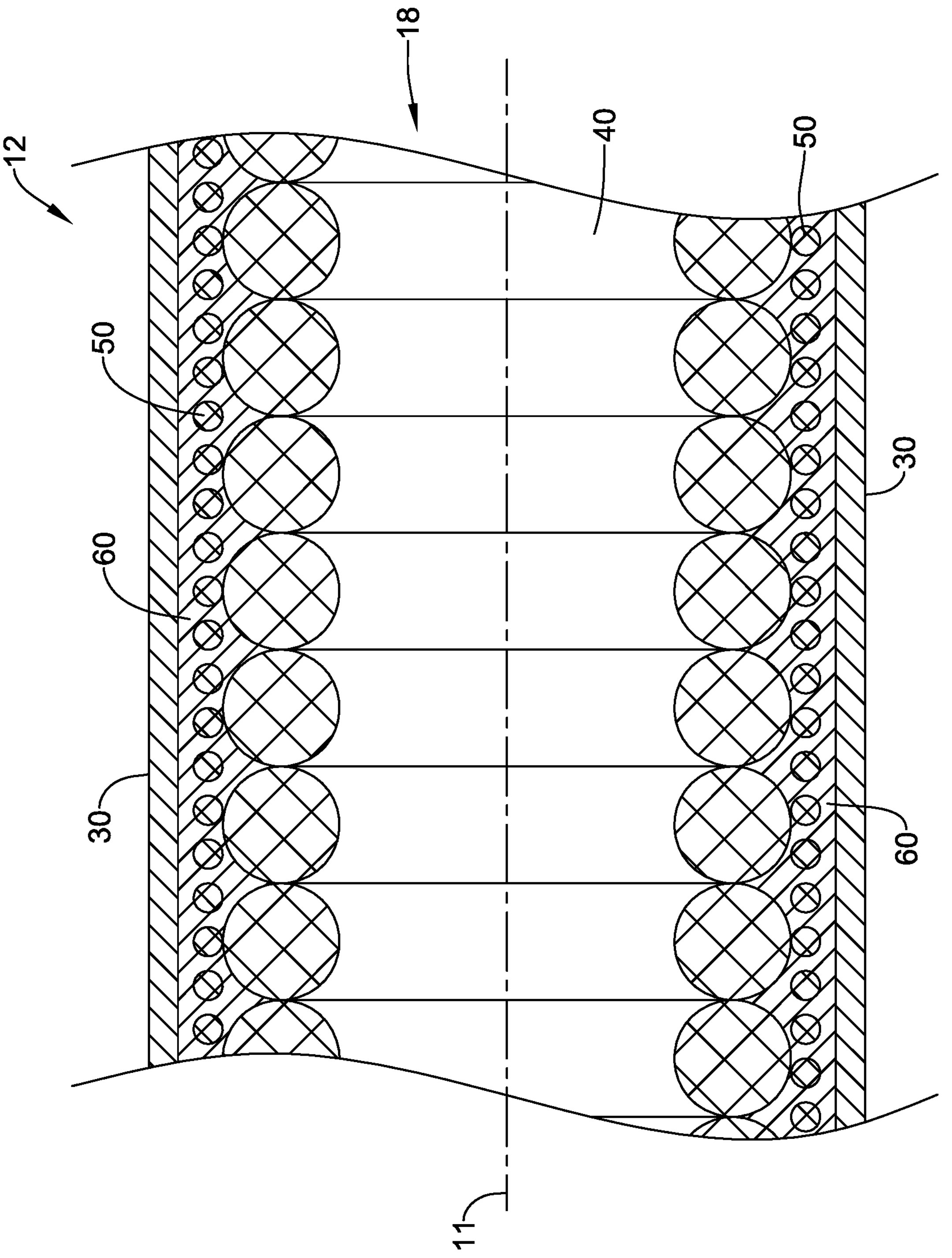
FIG. 2 is a partial cross-sectional view of an elongate tubular shaft of the example sheath of FIG. 1 in a straightened configuration.

FIG. 2 is a partial cross-sectional view of the elongate tubular shaft 12 of the sheath 10 in a straightened configuration. In at least some embodiments, the elongate tubular shaft 12 may be self-biased toward and/or may be at rest in the straightened configuration. The elongate tubular shaft 12 may include an outer jacket 30 forming an outer surface of the elongate tubular shaft 12. The outer jacket 30 may extend from the proximal portion 14 to the distal portion 16. In at least some embodiments, the outer jacket 30 may extend to and/or proximally from the distal end of the elongate tubular shaft 12. In some embodiments, the outer jacket 30 may extend along an entire length of the elongate tubular shaft 12. In some embodiments, the outer jacket 30 may be formed from a first material having a first modulus of elasticity.

In some embodiments, the outer jacket 30 may have a generally uniform diameter along a length of the elongate tubular shaft 12. The outer jacket 30 may be formed of one or more polymer and/or plastic materials along a length and/or thickness thereof. Some illustrative materials may include, but are not limited to polyether block amides (e.g., having a durometer in the range of 63D or greater), polyamides, polyurethanes, polyester/ethers, polyoxymethylene, nylons, blends, other high modulus polymers, etc. It is also understood that the outer jacket 30 may include materials other than polymers or plastics. For example, the outer jacket 30 may include polymers, metals, ceramics, composite materials, combinations thereof, and the like. Some additional suitable but non-limiting materials for the outer jacket 30 are described below.

The elongate tubular shaft 12 may further include a helical member 40 extending axially about the central longitudinal axis 11 of the elongate tubular shaft 12 from the proximal portion 14 to the distal portion 16. In some embodiments, the helical member 40 may extend to and/or proximally from the distal end of the elongate tubular shaft 12. In some embodiments, the helical member 40 may extend along the entire length of the elongate tubular shaft 12. In some embodiments, an inner surface and/or a radially inward facing surface of the helical member 40 may define the lumen 18 in the straightened configuration. In some embodiments, the helical member 40 may include and/or may be formed as a tightly wound coil. In some embodiments, adjacent windings of the helical member 40 may be in direct and/or physical contact with each other. In at least some embodiments, each winding of the helical member 40 may have a single and/or common inner diameter and/or inner radial extent. That is, each and every winding of the helical member 40 may have the same inner diameter and/or inner radial extent along the length of the helical member 40. In some embodiments, the helical member 40 may be formed with a circular cross-sectional shape, however, it is contemplated that the helical member 40 may have any cross-sectional shape desired, such as, but not limited to, rectangular, square, triangular, oblong, polygonal, etc.

In some embodiments, the helical member 40 may be formed from a metallic material, such as stainless steel, nickel-titanium alloy, or another suitable metallic material. In some embodiments, the helical member 40 may also be formed from polymers, metals, ceramics, composite materials, combinations thereof, and the like. Some additional suitable but non-limiting materials for the helical member 40 are described below.

The elongate tubular shaft 12 may include a braided support member 50 disposed about the helical member 40 from the proximal portion 14 to the distal portion 16. In some embodiments, the braided support member 50 may extend to and/or proximally from the distal end of the elongate tubular shaft 12. In some embodiments, the braided support member 50 may extend along the entire length of the elongate tubular shaft 12. In some embodiments, the braided support member 50 may include one or more filaments interwoven with each other around the central longitudinal axis 11 of the elongate tubular shaft 12 along a length of the braided support member 50. In some embodiments, the one or more filaments may form and/or define a plurality of cells. In some embodiments, the one or more filaments may be wires, threads, strands, etc. In some embodiments, the one or more filaments may define openings and/or interstices through a wall of the braided support member 50. Alternatively, in some embodiments, the braided support member 50 may be a monolithic structure formed from a single filament. In another alternative, the support member 50 may be a stent-like structure formed from a cylindrical tubular member, such as a single, cylindrical laser-cut nickel-titanium tubular member, in which the remaining (e.g., unremoved) portions of the tubular member form struts with openings and/or interstices defined therebetween.

In some embodiments, the braided support member 50 may be formed and/or disposed on an outer surface of the helical member 40. In some embodiments, the braided support member 50 may be formed and/or disposed in direct contact with the helical member 40. In some embodiments, the braided support member 50 may be formed and/or disposed directly on the helical member 40. In some embodiments, the braided support member 50 may substantially prevent relative radial moment of adjacent windings of the helical member 40 with respect to the central longitudinal axis 11 of the elongate tubular shaft 12. For example, the braided support member 50, alone and/or in conjunction with other elements and/or features described herein, may hold and/or maintain adjacent windings in line with each other and/or at a constant distance from the central longitudinal axis 11 of the elongate tubular shaft 12. Some suitable but non-limiting materials for the braided support member 50 and/or components or elements thereof, for example metallic materials and/or polymeric materials, are described below.

The elongate tubular shaft 12 may include a strain relief layer 60 extending from the proximal portion 14 to the distal portion 16. In some embodiments, the strain relief layer 60 may extend to and/or proximally from the distal end of the elongate tubular shaft 12. In some embodiments, the strain relief layer 60 may extend along the entire length of the elongate tubular shaft 12.

In some embodiments, the strain relief layer 60 may be formed from a second material having a second modulus of elasticity. In some embodiments, the second material may be different from the first material. In some embodiments, the second modulus of elasticity may be different from the first modulus of elasticity. In some embodiments, the second modulus of elasticity may be less than the first modulus of elasticity. In some embodiments, the second material may be more elastic than the first material.

In some cases, the strain relief layer 60 may be formed from an elastomeric material. An elastomeric material may be considered to be capable of achieving large and reversible elastic deformation. Some illustrative elastomeric materials may include, but are not limited to, urethane elastomers, elastomeric polyether block amides (e.g., elastomeric PEBAX®, having a durometer in the range of about 25D to about 35D), polysiloxane (e.g., silicone), styrene-butadiene copolymer, elastomeric polyamides, acrylonitrile-butadiene copolymer, chloroprene, natural polyisoprene, etc. The strain relief layer 60 may be highly flexible. It is contemplated that when formed from a flexible, elastomeric material, the strain relief layer 60 may handle high strain rates without fracture as described herein. Additionally, the strain relief layer 60 may smooth out the transitional geometry between the helical member 40 and the outer jacket 30. These features may create an effective strain relief between the helical member 40 and the outer jacket 30 thus decreasing the localized stress seen by the outer jacket 30. This may significantly improve the bend radius that the elongate tubular shaft 12 can achieve before fracturing. Some additional suitable but non-limiting materials for the strain relief layer 60, for example polymeric materials, are described below.

Figure 3:
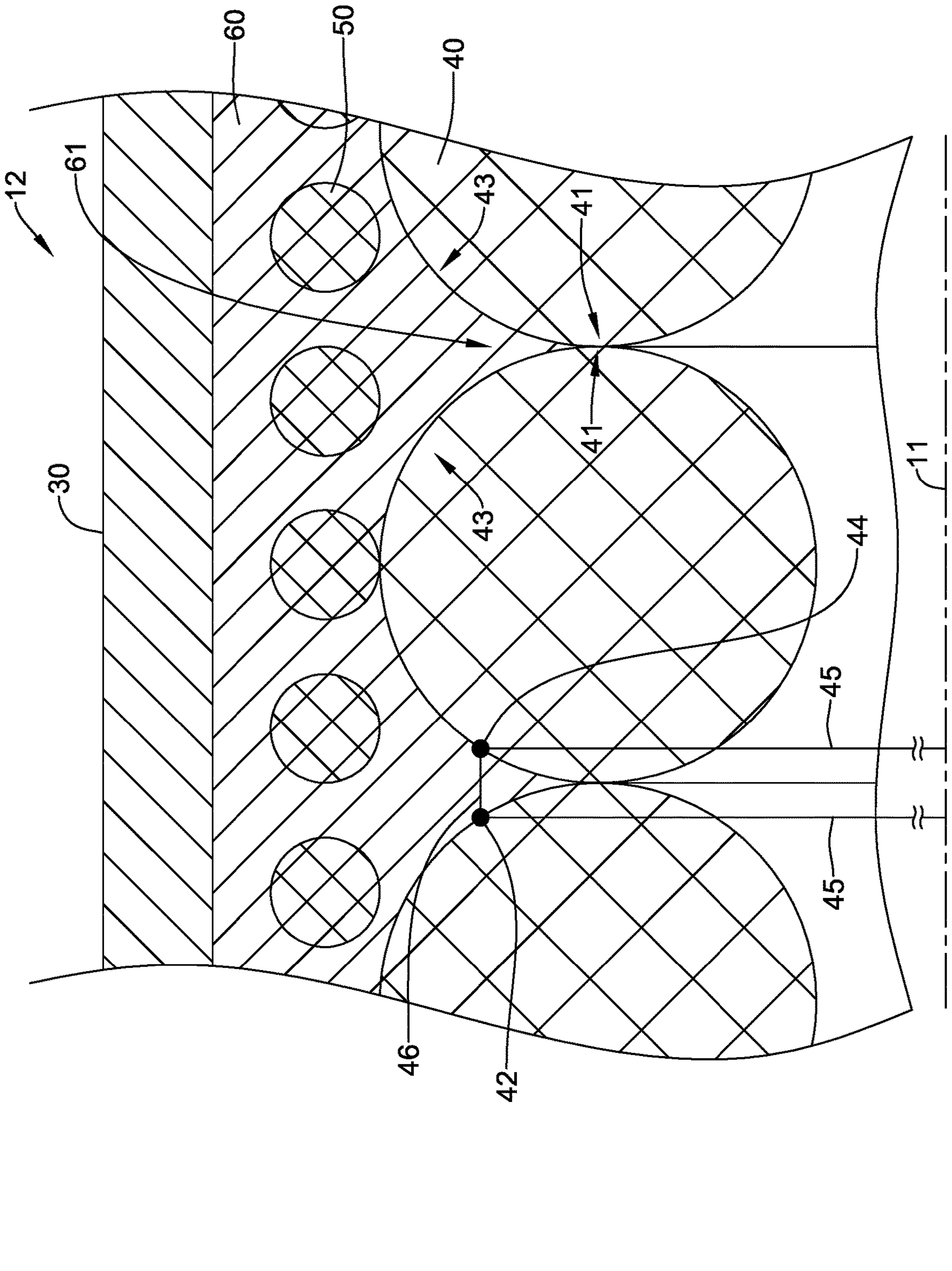
FIG. 3 is a detailed view of selected aspects of the elongate tubular shaft of FIG. 2.

In some embodiments, the strain relief layer 60 may be disposed between the outer jacket and the helical member 40. In some embodiments, the strain relief layer 60 may be disposed about the helical member 40 and radially inward of the outer jacket 30. In some embodiments, the strain relief layer 60 may be disposed radially outward of the helical member 40. In some embodiments, the strain relief layer 60 may be disposed on an outer surface of the helical member 40. In some embodiments, the elongate tubular shaft 12 may be devoid of the strain relief layer 60 radially inward of the helical member 40, as seen in FIG. 3. For example, adjacent windings of the helical member 40 in direct and/or physical contact with each other may substantially prevent the second material of the strain relief layer 60 from passing through the helical member and/or into the lumen 18 defined by the helical member 40.

In some embodiments, the braided support member 50 may be embedded within and/or surrounded by the strain relief layer 60. In some embodiments, the strain relief layer 60 may extend and/or pass through the openings and/or interstices between adjacent filaments of the braided support member 50. In some embodiments, the outer jacket 30 may be spaced apart from the braided support member 50 and/or the helical member 40 by the strain relief layer 60.

In some embodiments, at least a portion of the strain relief layer 60 may be disposed between portions of adjacent windings of the helical member 40 that are disposed radially outward of portions of the adjacent windings that are in direct and/or physical contact with each other. As an example only, first portions 41 of the helical member 40 may be in direct and/or physical contact with each other and second portions 43 of the helical member 40 may be disposed radially outward of the first portions 41 of the helical member 40, wherein at least a portion 61 of the strain relief layer 60 is disposed axially between the second portions 43 of adjacent windings of the helical member 40 and radially inward of an outermost radial extent of the adjacent windings of the helical member 40, as shown in FIG. 3.

The helical member 40 may include a first point 42 located a first distance 45 from the central longitudinal axis 11 of the elongate tubular shaft 12 and a second point 44 on an adjacent winding of the helical member 40 also located the first distance 45 from the central longitudinal axis 11 of the elongate tubular shaft 12. The first distance 45 may be measured perpendicular to the central longitudinal axis 11 of the elongate tubular shaft 12. In the straightened configuration, the first point 42 and the second point 44 on adjacent windings of the helical member 40 may be a first axial distance 46 apart as measured parallel to the central longitudinal axis 11 of the elongate tubular shaft 12. This relationship may be seen in FIG. 3 for example.

When the elongate tubular shaft 12 is bent or curved (e.g., FIG. 4) during use, such as when navigating tortuous vasculature, highly localized stress may develop in the strain relief layer 60 along the helical member 40 as adjacent windings of the helical member 40 are pulled apart axially along an outside curve or bend of the elongate tubular shaft 12. In the curved configuration, the strain relief layer 60 may cooperate and/or combine with the helical member 40 to define the lumen 18 along portions of the elongate tubular shaft 12 where adjacent windings of the helical member are pulled apart axially (e.g., along the outside curve). FIG. 5 illustrates relative levels of localized stress within the strain relief layer 60 as the elongate tubular shaft 12 is bent or curved. High stress zone 62 develops the highest relative level of localized stress and occurs closest (e.g., radially near) to the helical member 40 and/or the central longitudinal axis 11 of the elongate tubular shaft 12. Low stress zone 66 develops the lowest relative level of localized stress and occurs farthest (e.g., radially away) from the helical member 40 and/or the central longitudinal axis 11 of the elongate tubular shaft 12. Medium stress zone 64 develops a moderate relative level of localized stress and occurs between the high stress zone 62 and the low stress zone 66. The medium stress zone 64 serves as a transition zone between the high stress zone 62 and the low stress zone 66 within the strain relief layer 60.

Figure 4:
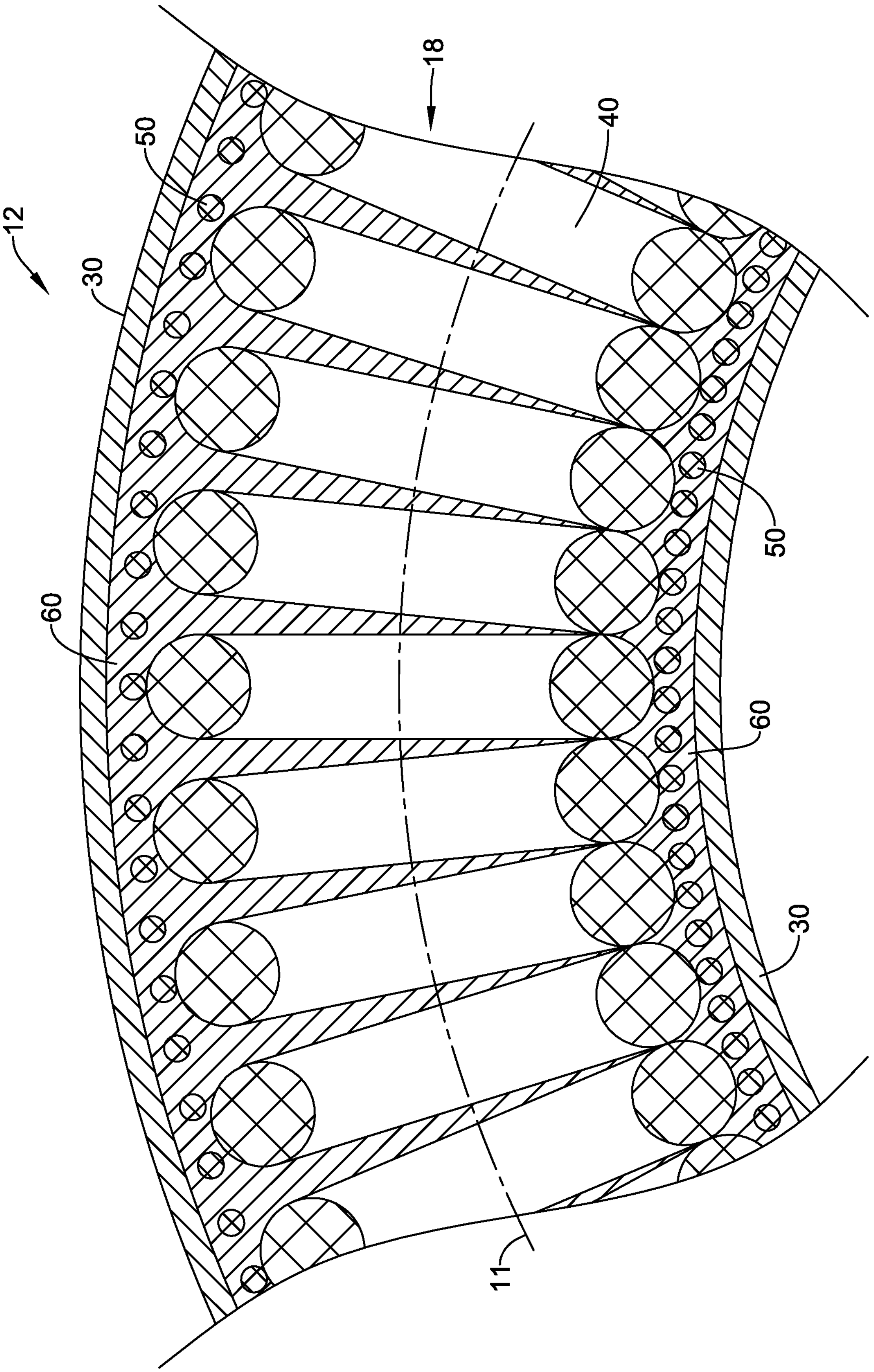
FIG. 4 is a partial sectional view of the elongate tubular shaft of FIGS. 1-2 in a curved configuration.
Figure 5:
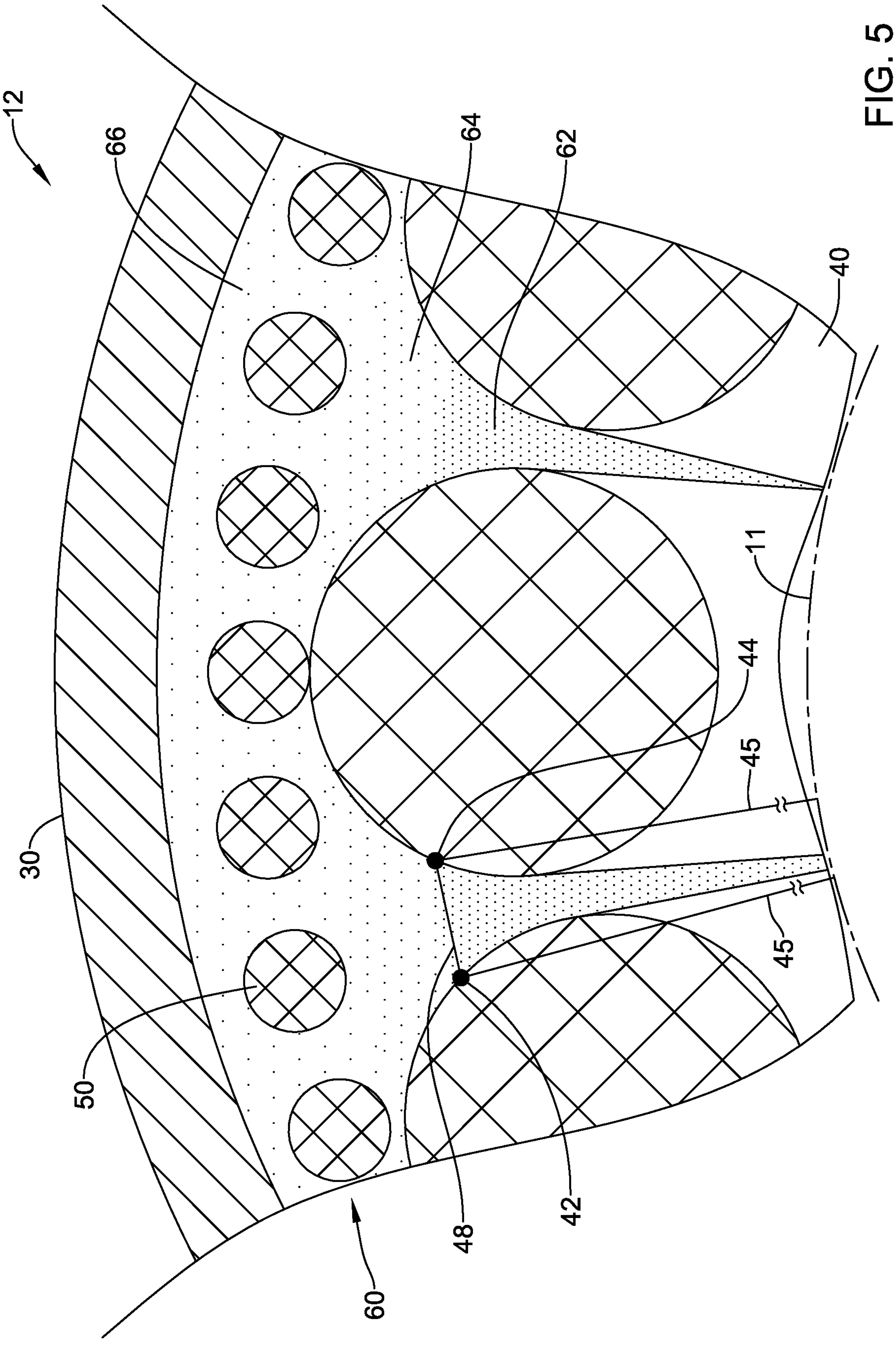
FIG. 5 is a detailed view of selected aspects of the elongate tubular shaft of FIG. 4.

It will be understood that the view shown in FIG. 5 is a three-dimensional view consistent with FIG. 4, in which the lumen 18 is devoid of the strain relief layer 60 and the strain relief layer 60 remains radially outward of the lumen 18 and/or the helical member 40, as clearly seen in FIGS. 2 and 3. As such, when the elongate tubular shaft 12 is bent, the strain relief layer 60 does not pass through the helical member 40 or between adjacent windings of the helical member 40 into the lumen 18. As discussed herein, the strain relief layer 60 is formed when the helical member is in a straightened configuration and adjacent windings of the helical member are in direct and/or physical contact with each other such that the strain relief layer 60 is prevented from passing through the helical member 40, between adjacent windings of the helical member 40, and/or into the lumen 18. This characteristic is maintained if and/or when the elongate tubular shaft 12 is bent during use.

A highly elastic material is needed to withstand the stresses formed within the strain relief layer 60 due to bending the elongate tubular shaft 12. However, highly elastic materials generally have a lower modulus of elasticity and less resistance to axial compression. As such, in some configurations, the outer jacket 30 would be formed of a material having a higher modulus of elasticity and greater resistance to axial compression than the strain relief layer 60 in order to maintain usability of the sheath 10. While not wishing to be bound by theory, if the strain relief layer 60 was formed of the first material and/or the same material as the outer jacket 30, the localized stress in the high stress zone 62 could cause the material of the strain relief layer 60 to fracture. However, the strain relief layer 60 may be configured to stretch and/or elongate without fracturing via the use of the second material that is different from the first material and/or has a lower modulus of elasticity than the first material. As shown in FIG. 5, in the curved configuration, the first point 42 and the second point 44 on adjacent windings of the helical member 40 may be a second axial distance 48 apart as measured parallel to the central longitudinal axis 11 of the elongate tubular shaft 12, wherein the second axial distance 48 is greater than the first axial distance 46 (e.g., FIG. 3). In some embodiments, the second axial distance 48 may be at least 100%, at least 150%, at least 200%, at least 250%, at least 300%, or more, greater than the first axial distance 46. In one example, the second axial distance 48 may be measured parallel to the central longitudinal axis 11 of the elongate tubular shaft 12, or along an arc in FIG. 5 because the elongate tubular shaft 12 is bent. In another example, the second axial distance 48 may be measured parallel to a line tangent to the central longitudinal axis 11 of the elongate tubular shaft 12 and passing through both the first point 42 and the second point 44. In each case, the second axial distance 48 is greater than the first axial distance 46 along and/or adjacent to the outside curve or bend of the elongate tubular shaft 12.

The configurations of the current disclosure may permit the use of a first material for the outer jacket 30 that has a lower modulus of elasticity and greater flexibility than a sheath lacking the helical member 40 because the helical member 40 substantially prevents axial compression of the elongate tubular shaft 12 and/or the outer jacket 30. The direct and/or physical contact between adjacent windings of the helical member 40 effectively provides the elongate tubular shaft 12 with an axially incompressible configuration, thereby negating requirements for the outer jacket 30 to substantially support the elongate tubular shaft 12 in axial compression. As a result, the elongate tubular shaft 12 may be prevented from bending or deforming, developing internal spring force, and/or developing internal whipping force.

In at least some embodiments, the braided support member 50 may also play a role in preventing axial compression of the elongate tubular shaft 12. As discussed herein, the braided support member 50, alone and/or in conjunction with other elements and/or features described herein, may hold and/or maintain adjacent windings of the helical member 40 in line with each other and/or at a constant distance from the central longitudinal axis 11 of the elongate tubular shaft 12. As such, the braided support member 50 substantially prevents adjacent windings from shifting laterally and/or radially relative to each other and/or the central longitudinal axis 11 of the elongate tubular shaft 12, which would permit some degree of axial shortening and/or axial compression of the outer jacket 30 and/or the elongate tubular shaft 12.

Figure 6:
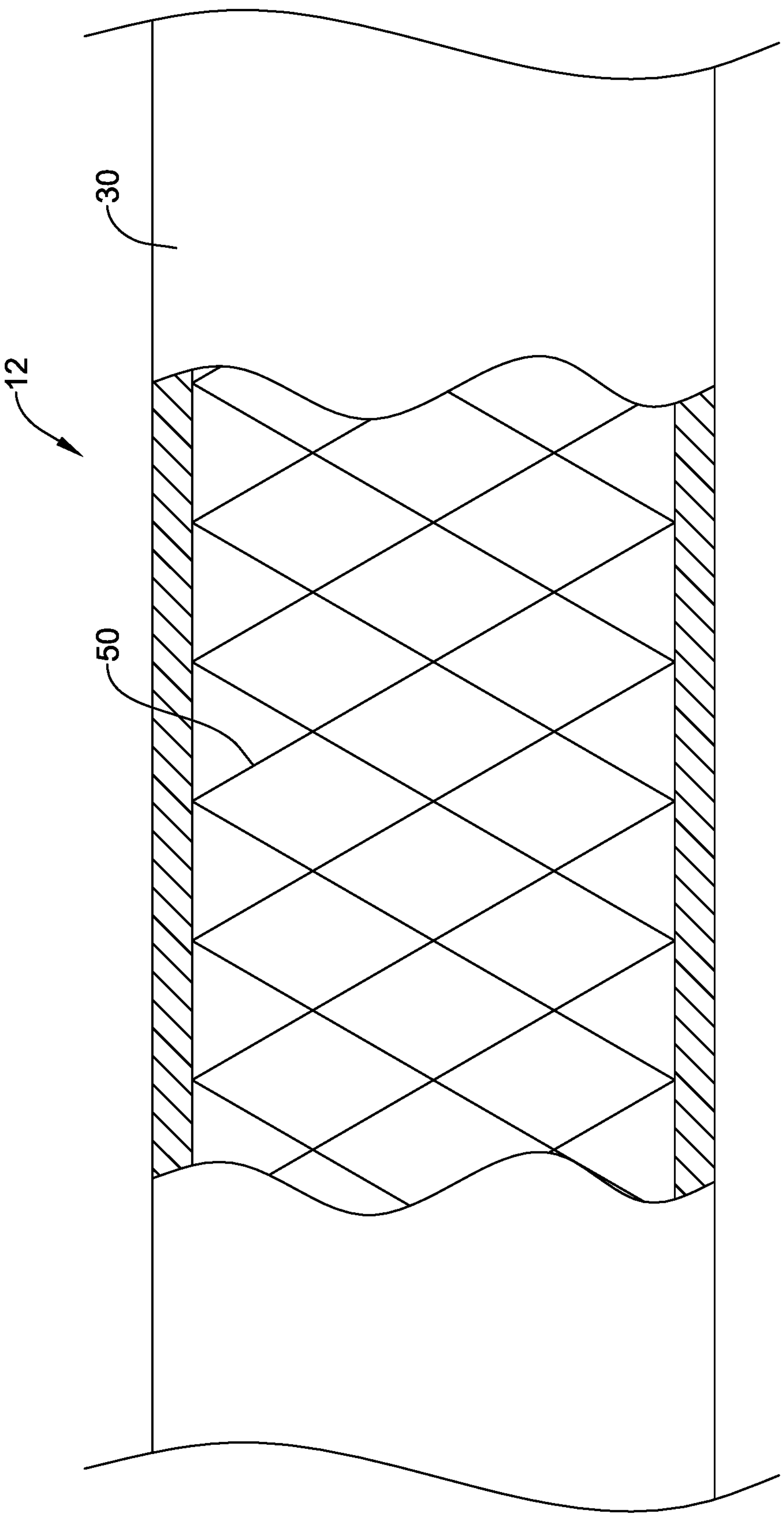
FIG. 6 is a partial cutaway view illustrating selected aspects of the elongate tubular shaft of FIGS. 1-5.
Figure 7:
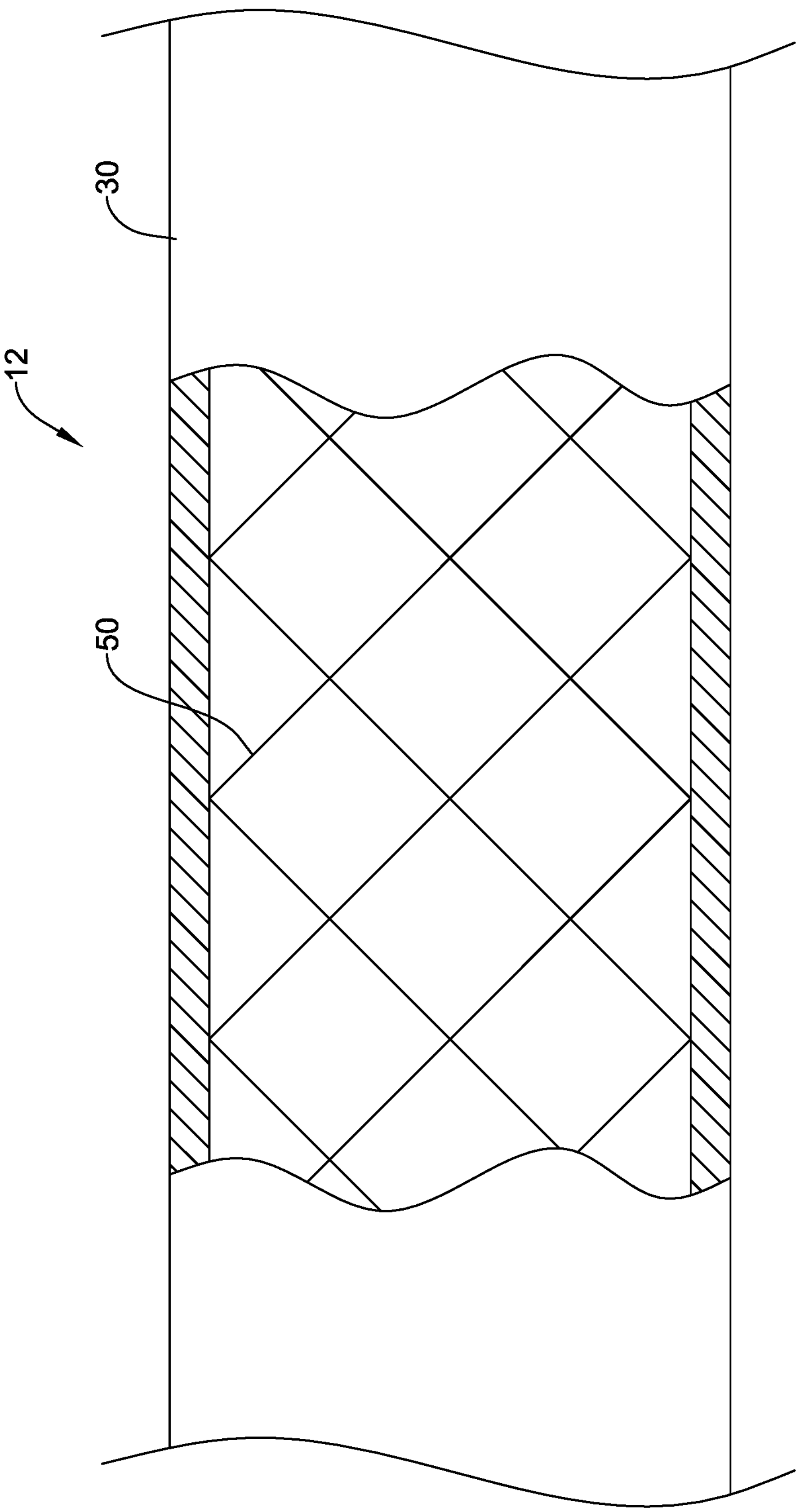
FIG. 7 is a partial cutaway view illustrating selected aspects of the elongate tubular shaft of FIGS. 1-5.

The braided support member 50 also adds tensile strength to the elongate tubular shaft 12, thereby limiting and/or minimizing elongation of the elongate tubular shaft 12 under tension, and increased torque transmission between the proximal end and/or the proximal portion 14 of the elongate tubular shaft 12 and the distal end and/or the distal portion 16 of the elongate tubular shaft 12. FIGS. 6 and 7 are partial cutaway views illustrating example configurations of the braided support member 50 disposed over the helical member 40 (not shown for clarity), wherein at least a portion of the outer jacket 30 has been cut away. Relatively speaking, FIG. 6 illustrates a higher PIC (per inch crosses) count braid configuration and FIG. 7 illustrates a lower PIC count braid configuration. Braid angle, defined as an angle of the filaments relative to a plane disposed orthogonal to the central longitudinal axis 11 of the elongate tubular shaft 12, may have a direct relationship with PIC count while also affecting flexibility and longitudinal stiffness characteristics of the elongate tubular shaft 12. Relatively speaking, in the configuration of FIG. 6, the braid angle is lower (e.g., the one or more filaments oriented less axially), flexibility is increased, and tensile strength is decreased, while in the configuration of FIG. 7, the braid angle is higher (e.g., the one or more filaments oriented more axially), flexibility is decreased, and tensile strength is increased.

In the braided support member 50, the one or more filaments may comprise two filaments, three filaments, four filaments, five filaments, six filaments, seven filaments, eight filaments, 12 filaments, 16 filaments, 24 filaments, 36 filaments, 48 filaments, etc. Other configurations are also contemplated. Furthermore, in some embodiments, each filament may comprise multiple strands. The number of filaments present in the braided support member 50, as well as the number of strands within each filament, may affect flexibility and tensile characteristics of the braided support member 50. For example, increasing the number of filaments may increase the tensile strength of the braided support member 50 if the braid angle is kept constant. However, the increased material in the braided support member 50 from increasing the number of filaments may also reduce flexibility. The inverse of this relationship is also true. Similarly, increasing the size and/or diameter of the filaments may increase the tensile strength of the braided support member 50 if the braid angle is kept constant. Again, the increased material in the braided support member 50 from increasing the number of filaments may reduce flexibility, and the inverse of this relationship is also true. As such, the configuration of the braided support member 50 is selected carefully to ensure that the elongate tubular shaft 12 provides the desired functional characteristics. Different configurations of the braided support member 50 may permit different materials to be selected for the outer jacket 30 while maintaining the desired functional characteristics of the elongate tubular shaft 12 overall. For example, use of the helical member 40 and the braided support member 50 may substantially relieve the outer jacket 30 from supporting the elongate tubular shaft 12 under compressive forces and/or from carrying compressive loads. As such, the first material of the outer jacket 30 in the sheath 10 may be made from a more flexible material while supporting the same compressive forces and/or loads as an otherwise identical sheath 10 lacking the helical member 40 and the braided support member 50.

Figure 8:
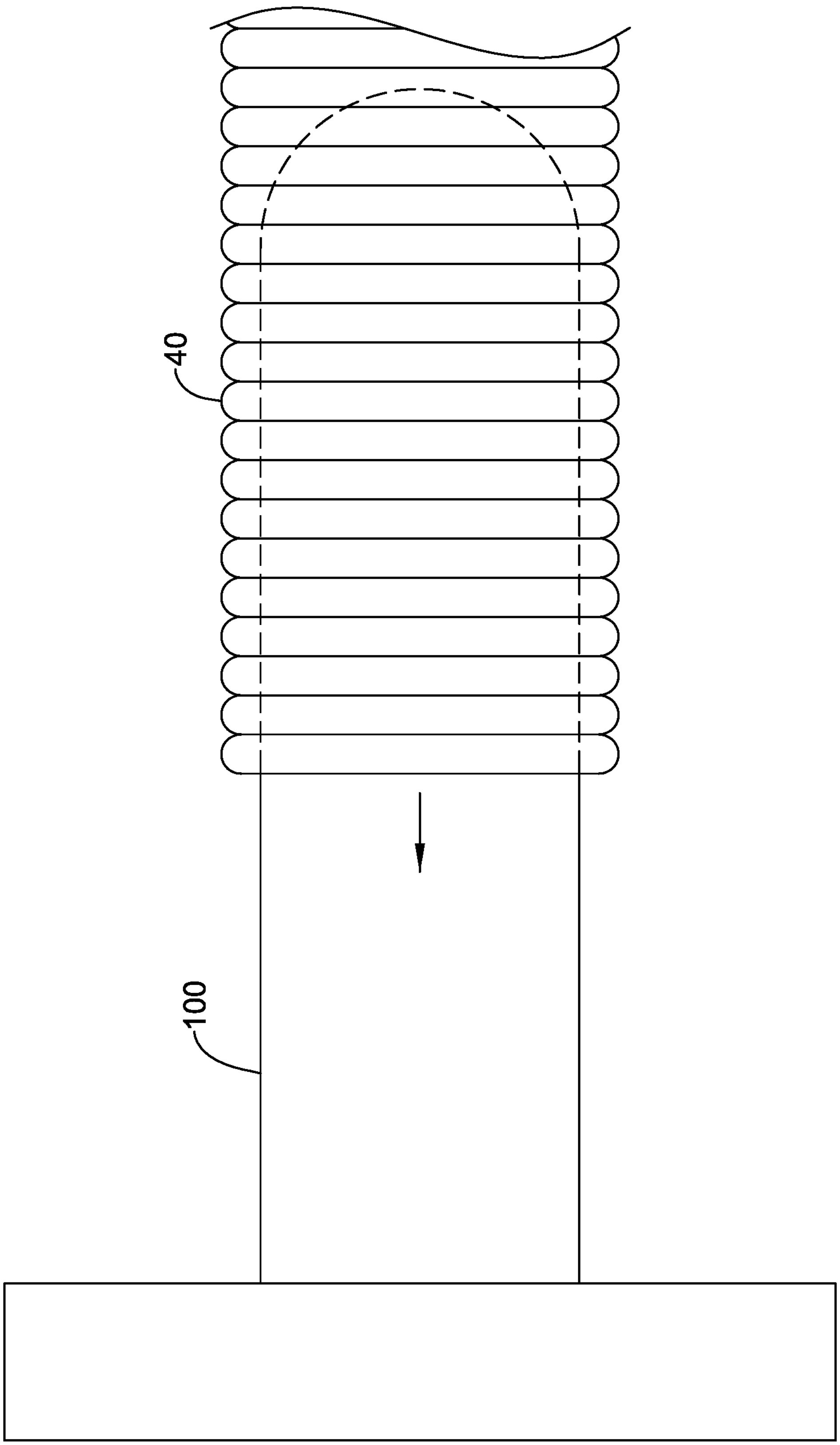
FIGS. 8-11 illustrate selected aspects of a method of manufacturing the elongate tubular shaft of FIGS. 1-7.

FIGS. 8-11 illustrates selected aspects of a method of manufacturing the elongate tubular shaft 12 of the sheath 10. As seen in FIG. 8, the method may include positioning the helical member 40 onto an elongate mandrel 100 with adjacent windings of the helical member 40 in direct and/or physical contact with each other. The helical member 40 may be self-biased toward an axially compressed configuration in which the adjacent windings of the helical member 40 are in direct and/or physical contact with each other. The elongate mandrel 100 may include a smooth outer surface having an outer diameter and/or an outer radial extent approximately equal to an inner diameter and/or an inner radial extent of the helical member 40.

Figure 9:
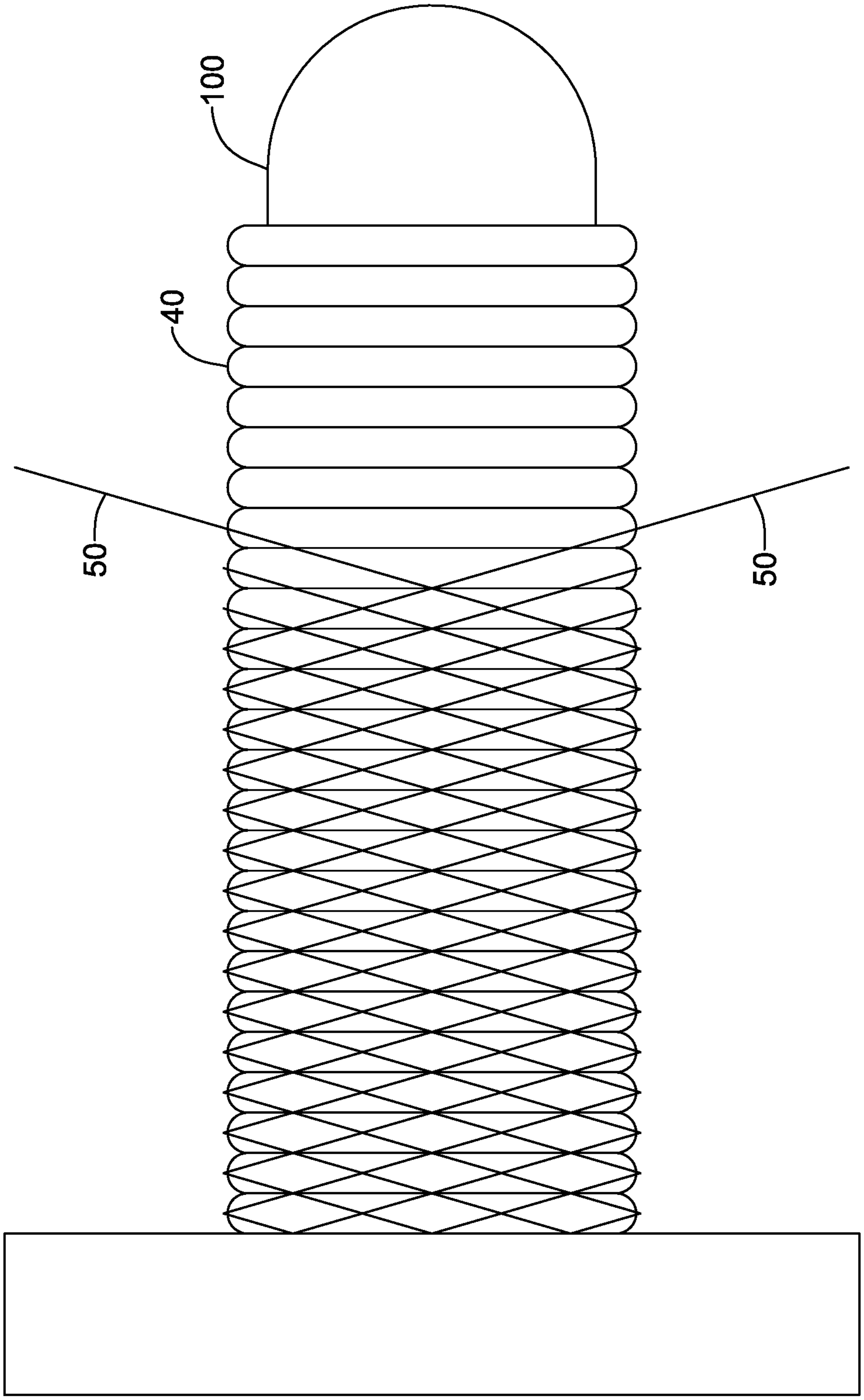

As seen in FIG. 9, the method may include interweaving the braided support member 50 on and/or onto an outer surface of the helical member 40. During processing, the elongate mandrel 100 and the helical member 40 positioned thereon may be put through a braiding machine (not shown) such that the braided support member 50 is wound directly onto the outer surface of the helical member 40. As such, the braided support member 50 may be in direct contact with the helical member 40. When constructed in this manner, the braided support member 50 may substantially prevent relative radial movement of adjacent windings of the helical member 40 with respect to the central longitudinal axis 11 of the elongate tubular shaft 12 after the elongate tubular shaft 12 has been removed from the elongate mandrel 100.

Figure 10:
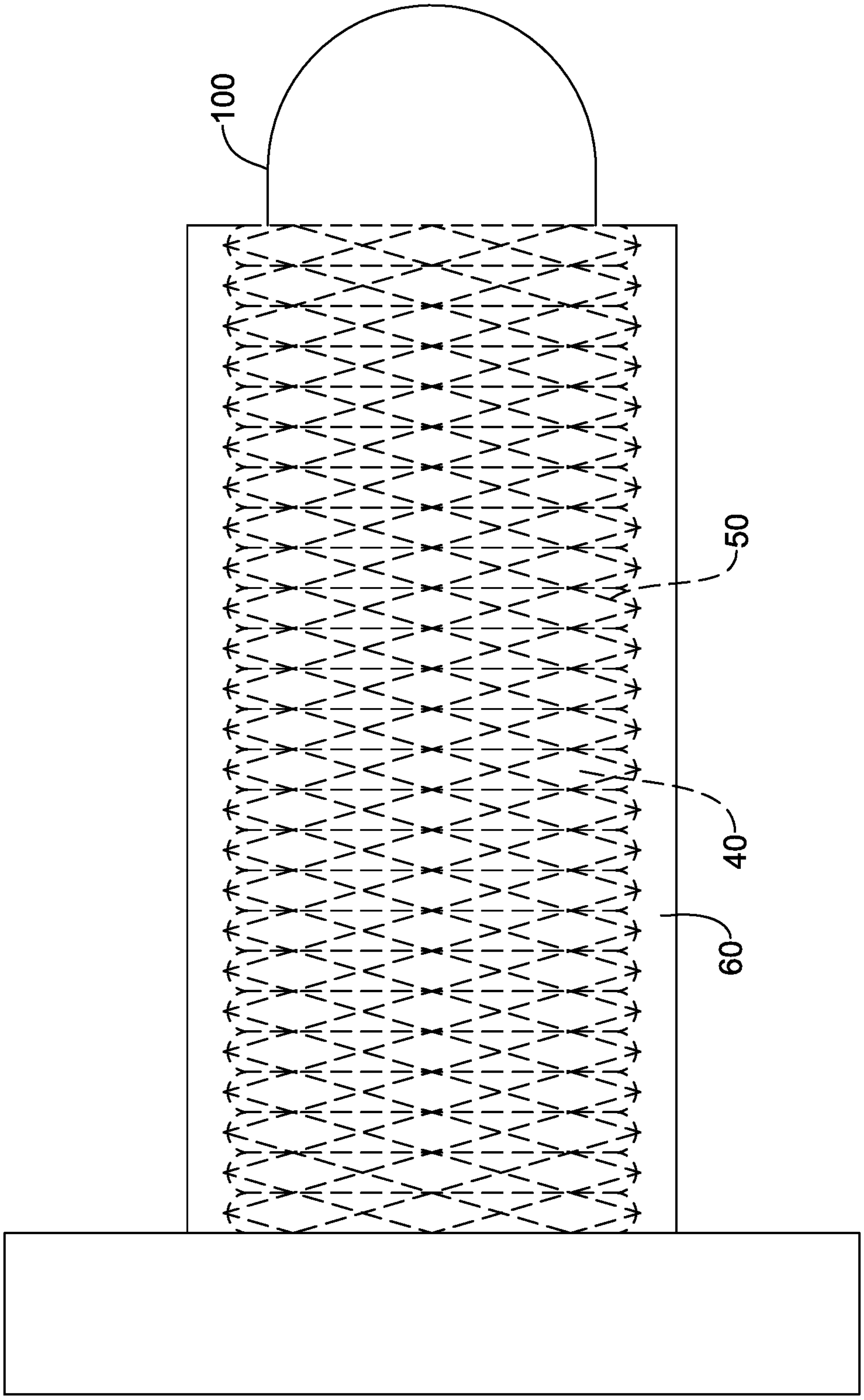

FIG. 10 illustrates the method may include disposing an elastomeric material (e.g., the second material) over the braided support member 50 and the helical member 40 to form the strain relief layer 60. In at least some embodiments, disposing the elastomeric material (e.g., the second material) over the braided support member 50 and the helical member 40 may include melting the elastomeric material (e.g., the second material) such that the elastomeric material (e.g., the second material) flows through openings and/or interstices of the braided support member 50 and against the outer surface of the helical member 40. In some embodiments, the elastomeric material (e.g., the second material) may be extruded over the braided support member 50 and the helical member 40. In some embodiments, the elastomeric material (e.g., the second material) may be co-molded, over-molded, and/or injection molded over the braided support member 50 and the helical member 40. Other means of forming the strain relief layer 60 are also contemplated. The elongate tubular shaft 12 may be devoid of the elastomeric material (e.g., the second material) radially inward of the helical member 40, as discussed herein, because the elastomeric material (e.g., the second material) fails to and/or cannot penetrate between adjacent windings of the helical member 40. The strain relief layer 60 may be formed with a generally uniform outer diameter and/or outer radial extent along its length.

Figure 11:
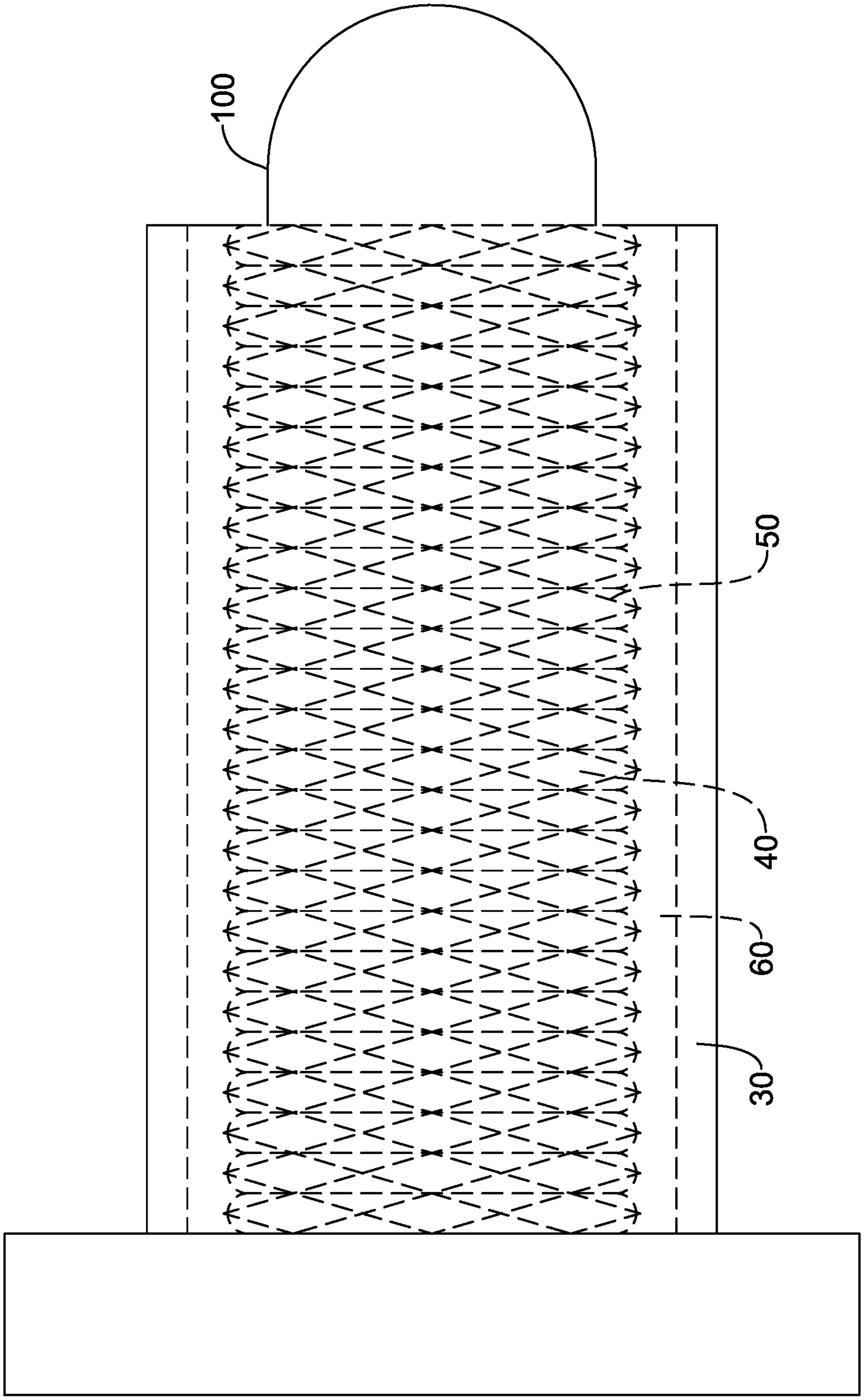

As seen in FIG. 11, the method may include disposing the outer jacket 30 over the strain relief layer 60 to form the outer surface of the elongate tubular shaft 12. In some embodiments, the outer jacket 30 may be formed from a different material (e.g., the first material) than the strain relief layer 60. In some embodiments, disposing the outer jacket 30 over the strain relief layer 60 may include melting the different material (e.g., the first material) of the outer jacket 30 over and/or onto the elastomeric material (e.g., the second material) of the strain relief layer 60. In some embodiments, the different material (e.g., the first material) may be extruded over the strain relief layer 60. In some embodiments, the different material (e.g., the first material) may be co-molded, over-molded, and/or injection molded over the strain relief layer 60. In some embodiments, the different material (e.g., the first material) of the outer jacket 30 may be pre-formed and then heat shrunk onto the elastomeric material (e.g., the second material) of the strain relief layer 60. Other means of forming the outer jacket 30 are also contemplated. In some embodiments, disposing the outer jacket 30 over the strain relief layer 60 may include bonding the different material (e.g., the first material) of the outer jacket 30 to the elastomeric material (e.g., the second material) of the strain relief layer 60. In some embodiments, the outer jacket 30 may be formed over or positioned on top of the strain relief layer 60 such that an inner diameter and/or inner radial extent of the outer jacket 30 is approximately equal to the outer diameter and/or outer radial extent of the strain relief layer 60. In some embodiments, after disposing the outer jacket 30 over the strain relief layer 60, no radial space is present between the strain relief layer 60 and the outer jacket 30.

The materials that can be used for the various components of the sheath 10 (and/or other systems or components disclosed herein) and the various elements thereof disclosed herein may include those commonly associated with medical devices. For simplicity purposes, the following discussion makes reference to the sheath, etc. However, this is not intended to limit the devices and methods described herein, as the discussion may be applied to other elements, members, components, or devices disclosed herein, such as, but not limited to, the elongate tubular shaft 12, the outer jacket 30, the helical member 40, the braided support member 50, the strain relief layer 60, etc. and/or elements or components thereof.

In some embodiments, the sheath and/or components thereof may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof, and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the sheath and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the sheath. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the sheath to achieve the same result.

In some embodiments, a degree of Magnetic Resonance Imaging (MRI) compatibility is imparted into the sheath. For example, the sheath and/or components or portions thereof, may be made of a material that does not substantially distort the image and create substantial artifacts (e.g., gaps in the image). Certain ferromagnetic materials, for example, may not be suitable because they may create artifacts in an MRI image. The sheath or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the sheath and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the sheath may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the sheath may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, antithrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. An elongate tubular shaft having a lumen extending from a proximal portion to a distal portion, the elongate tubular shaft comprising:

an outer jacket forming an outer surface of the elongate tubular shaft, the outer jacket being formed from a first material having a first modulus of elasticity;

a helical member extending from the proximal portion to the distal portion, the helical member comprising a plurality of adjacent windings in physical contact with each other when the elongate tubular shaft is in a straightened configuration;

a braided support member disposed about the helical member and in physical contact with the helical member, the helical member and braided support member providing column strength to the elongate tubular shaft; and a strain relief layer formed from a second material having a second modulus of elasticity less than the first modulus of elasticity;

wherein the braided support member is embedded within the strain relief layer and the strain relief layer is disposed about the helical member.

2. The elongate tubular shaft of claim 1, wherein the strain relief layer comprises an elastomeric material.

3. The elongate tubular shaft of claim 1, wherein the strain relief layer comprises a urethane elastomer or an elastomeric polyether block amide.

4. The elongate tubular shaft of claim 1, wherein the braided support member prevents relative radial movement of adjacent windings of the helical member with respect to a central longitudinal axis of the elongate tubular shaft.

5. The elongate tubular shaft of claim 1, wherein the helical member is formed from a metallic material.

6. The elongate tubular shaft of claim 1, wherein the outer jacket is spaced apart from the braided support member and the helical member by the strain relief layer.

7. The elongate tubular shaft of claim 1, wherein the elongate tubular shaft is devoid of the strain relief layer radially inward of the helical member.

8. An elongate tubular shaft having a lumen extending from a proximal portion to a distal portion, the elongate tubular shaft comprising:

an outer jacket forming an outer surface of the elongate tubular shaft, the outer jacket being formed from a first material;

a helical member extending axially about a central longitudinal axis of the elongate tubular shaft from the proximal portion to the distal portion, wherein a radially inward facing surface of the helical member defines the lumen;

a braided support member disposed on and in physical contact with an outer surface of the helical member; and a strain relief layer formed from a second material different from the first material;

wherein the strain relief layer is disposed about the helical member and radially inward of the outer jacket.

9. The elongate tubular shaft of claim 8, wherein the second material is more elastic than the first material.

10. The elongate tubular shaft of claim 8, wherein adjacent windings of the helical member are in contact with each other.

11. The elongate tubular shaft of claim 10, wherein at least a portion of the strain relief layer is disposed between portions of adjacent windings of the helical member that are disposed radially outward of portions of the adjacent windings that are in contact with each other.

* * * * *